United States Patent [19]

Hunsucker

[11] 4,007,274

[45] Feb. 8, 1977

[54] METHOD OF CONTROLLING THE GROWTH OF BACTERIA AND FUNGI USING SUBSTITUTED TETRAHYDRO-S-TRIAZIN-2(1H)-ONE COMPOUNDS

[75] Inventor: Jerry Hoyt Hunsucker, Terre Haute, Ind.

[73] Assignee: IMC Chemical Group, Inc., Terre Haute, Ind.

[22] Filed: Mar. 22, 1976

[21] Appl. No.: 669,356

[52] U.S. Cl. .......................... 424/249; 260/248 NS
[51] Int. Cl.² ........................................... A01N 9/22
[58] Field of Search .............. 424/249; 260/248 NS

[56] References Cited

UNITED STATES PATENTS

| 2,901,463 | 8/1959 | Hurwitz | 260/248 NS |
|---|---|---|---|
| 2,950,553 | 8/1960 | Hurwitz | 260/248 NS |
| 3,501,467 | 3/1970 | Shay et al. | 260/248 |
| 3,915,970 | 10/1975 | Limaye et al. | 424/249 |

Primary Examiner—Albert T. Meyers
Assistant Examiner—Allen J. Robinson
Attorney, Agent, or Firm—Robert H. Dewey; Howard E. Post

[57] ABSTRACT

A method of controlling the growth of bacteria and fungi by applying to the environment inhabited by them a compound represented by the formula

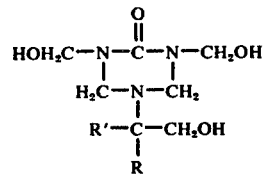

where R and R' are hydrogen, methyl, hydroxymethyl or ethyl and can be the same or different.

9 Claims, No Drawings

METHOD OF CONTROLLING THE GROWTH OF BACTERIA AND FUNGI USING SUBSTITUTED TETRAHYDRO-S-TRIAZIN-2(1H)-ONE COMPOUNDS

BACKGROUND OF THE INVENTION

This invention relates to a method of controlling the growth of bacteria and fungi. In a particular aspect, this invention relates to a method of controlling the growth of bacteria and fungi by applying thereto, and to the environment inhabited by them, certain members of the class of triazones.

Although many anti-bacterial and anti-fungal agents are known, many of the previously-used ones have been found to have disadvantages, such as lack of stability, ability of the organism to develop resistance, contribution to environmental pollution, development of toxic reactions by individuals inadvertently exposed to them, etc. Accordingly, there is an ever-present need for new anti-bacterial and anti-fungal agents.

SUMMARY OF THE INVENTION

It is an object of this invention to provide a method of controlling the growth of bacteria and fungi.

It is another object of this invention to provide a method of controlling the growth of bacteria and fungi by applying thereto, and to the environment inhabited by them, certain members of the class of triazones.

Other objects of this invention will be apparent to those skilled in the art from the disclosure herein.

It is the discovery of this invention that the growth of many bacteria and fungi is controlled by applying to them, or to the environment inhabited by them, a triazone represented by the formula (I)

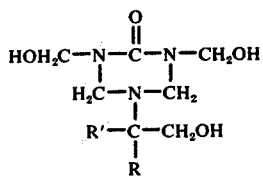

where R and R' can be hydrogen, methyl, hydroxymethyl, or ethyl and can be the same or different.

DETAILED DISCUSSION

The compounds used in the practice of this invention are prepared by reacting dimethylol urea, which is a known compound, commercially available, with an alkanolamine represented by the formula

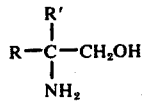

where R and R' have the same meanings defined above, and condensing the product so obtained with formaldehyde to yield a compound represented by formula I, above. The preferred compound is that obtained from 2-amino-2-methyl-1-propanol.

Suitable alkanolamines represented by the above formula include ethanolamine, 2-amino-propanol, 2-amino-2-methyl-1-propanol, 2-amino-1-butanol, 2-amino-2-methyl-1,3-propanediol, 2-amino-2-ethyl-1,3-propanediol, and 2-amino-2-hydroxymethyl-1,3-propanediol. These alkanolamines are all commercially available and the usual commercial grades are suitable for the practice of this invention.

In general, the compounds are prepared by reacting dimethylol urea with the alkanolamine in a mole ratio of about 1:1. The reaction proceeds at room temperature, but should be heated to about 95°–100° C to finish it. The product is then stripped of volatiles at reduced pressure, e.g. 50° at 20 mm. It is then cooled to room temperature and 2 moles of formaldehyde are added. Condensation proceeds at room temperature, but heat can be applied to accelerate the reaction if preferred. The product so obtained is usually in aqueous solution (if aqueous formaldehyde is used) and the solution is suitable for use in the practice of this invention.

The formaldehyde used in the practice of this invention is preferably the ordinary 37% aqueous formaldehyde of commerce. However, the 44% grade is equally useful as are the solutions of formaldehyde in the lower alkanols. Formaldehyde from a formaldehyde source can also be used if desired.

The compounds of this invention can be used in any manner known in the art, of which there are many. Generally they will be used in aqueous systems as preservatives, e.g. in cutting oils, protein adhesives, latex paints and the like. When preferred, however, they can be applied in the form of dusts, sprays and the like.

The compounds useful in the practice of the present invention are generally effective within the range of about 50–2000 ppm or more. Depending on the degree of infestation and the organism anticipated, it is generally preferred to employ the compounds at the higher concentrations of 1000–3000 ppm.

The invention will be better understood with reference to the following examples. It is understood, however, that the examples are intended only to illustrate the invention, and it is not intended that the invention be limited thereby.

EXAMPLE 1

Dimethylol urea was prepared by delivering to a reaction vessel 60 g of urea (1 mole) and 162 g of 37% aqueous formaldehyde (2 moles). The reaction vessel was fitted with an agitator and thermometer. The pH was adjusted to 7.0 with sodium hydroxide. The mixture was stirred well, then allowed to stand at room temperature for about 3 hours. Then 89 g of 2-amino-2-methyl-1-propanol, 1 mole, was added while maintaining a temperature of 5°–15° C. The mixture was then allowed to warm slowly to room temperature where it was maintained about an hour. It was then heated at 95°–100° C for about 2 hours. Volatiles were stripped by vacuum distillation until the pot temperature reached 50° at 20 mm.

The reaction mixture was cooled to room temperature and 162 g of 37% formaldehyde (2 moles) was added. It was agitated for about 3 hours at room temperature and allowed to stand overnight. The resulting product contained about 64% of tetrahydro-1,3-bis(hydroxymethyl)-5-(2-hydroxy-1,1-dimethylethyl)-1,3,5-triazin-2(1H)-one in water.

The compound was tested for anti-bacterial and anti-fungal activity by determining the minimum inhibitory concentration range for 9 bacterial and 8 fungi. In the range given below, the lower figure is the highest concentration at which growth occurred and the higher figure is the lowest concentration tested at which no growth of organism occurred. The results are as follows:

| Bacteria | Minimum Inhibitory Concentration, ppm |
| --- | --- |
| Bacillus subtilis | 500–1000 |
| Staphylococcum aureus | 500–1000 |
| Streptococcus faecalis | 1000–2000 |
| Sarcina lutea | 1000–2000 |
| Escherichia coli | 1000–2000 |
| Aerobacter aerogenes | 1000–2000 |
| Pseudomonas aeruginosa | 500–1000 |
| Salmonella typhi | 250–500 |
| Desulfovibrio aestuarii | 500–1000 |

| Fungi | Minimum Inhibitory Concentration, ppm |
| --- | --- |
| Cladosporium herbarum | 1000–2000 |
| Cephalosporium species | 32.25–64.5 |
| Trichophyton mentagrophytes | 125–250 |
| Aspergillus niger | 500–1000 |
| Aureobasidium pullulans | 500–1000 |
| Fusarium moniliforme | >2000 |
| Saccharomyces cerevisiae | 64.5–125 |
| Candida albicans | 125–250 |

It is determined that the product is useful as a preservative in latex paints and cutting oils.

EXAMPLE 2

The experiment of Example 1 is repeated in all essential details except that ethanolamine is substituted for 2-amino-2-methyl-1-propanol on an equimolar basis. The product obtained is tetrahydro-5-(2-hydroxyethyl)-1,3-bis (hydroxymethyl)-1,3,5-triazin-2(1H)-one. It is effective as a preservative at concentrations of 500 ppm to 3000 ppm or more.

EXAMPLE 3

The experiment of Example 1 is repeated in all essential details except that 2-amino-1-butanol is substituted for 2-amino-2-methyl-1-propanol on an equimolar basis. The product obtained is tetrahydro-1,3-bis(hydroxymethyl)-5-[1-(hydroxymethyl)propyl]-1,3,5-triazin-2(1H)-one. It is effective as a preservative at concentrations of 500 ppm to 3000 ppms or more.

EXAMPLE 4

The experiment of Example 1 is repeated in all essential details except that 2-amino-2-methyl-1,3-propanediol is substituted for 2-amino-2-methyl-1-propanol on an equimolar basis. The product obtained is tetrahydro-1,3-bis (hydroxymethyl)-5-[1,1-bis(hydroxymethyl)ethyl]-1,3,5-triazin-2(1H)-one. It is effective as a preservative at concentrations of 500 ppm to 3000 ppm or more.

EXAMPLE 5

The experiment of Example 1 is repeated in all essential details except that 2-amino-2-ethyl-1,3-propanediol is substituted for 2-amino-2-methyl-1-propanol on an equimolar basis. The product obtained is tetrahydro-1,3-bis(hydroxymethyl)-5-[1,1-bis(hydroxymethyl)propyl]-1,3,5-triazin-2(1H)-one. It is effective as a preservative at concentrations of 500 ppm to 3000 ppm or more.

EXAMPLE 6

The experiment of Example 1 is repeated in all essential details except that 2-amino-2-hydroxymethyl-1,3-propanediol is substituted for 2-amino-2-methyl-1-propanol on an equimolar basis. The product obtained is tetrahydro-1,3-bis(hydroxymethyl)-5-[2-hydroxy-1,1-bis(hydroxymethyl)ethyl]-1,3,5-triazin-2(1H)-one. It is effective as a preservative at concentrations of 500 ppm to 3000 ppm or more.

EXAMPLE 7

The experiment of Example 1 is repeated in all essential details except that 2-amino-1-propanol is substituted for 2-amino-2-methyl-1-propanol on an equimolar basis. The product obtained is tetrahydro-1,3-bis(hydroxymethyl)-5-(2-hydroxy-1-methylethyl)-1,3,5-triazin-2(1H)-one. It is effective as a preservative at concentrations of 500 ppm to 3000 ppm or more.

I claim:

1. A method of controlling the growth of bacteria or fungi by applying to them or to the environment inhabited by them an anti-bacterial or anti-fungal amount of from 50 to 3000 ppm of a compound represented by the formula

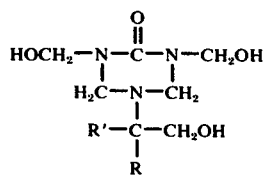

wherein R and R' are hydrogen, methyl, hydroxymethyl or ethyl and can be the same or different.

2. The method of claim 1 wherein R is hydrogen.
3. The method of claim 1 wherein R is methyl.
4. The method of claim 1 wherein R is ethyl.
5. The method of claim 1 wherein R is hydroxymethyl.
6. The method of claim 1 wherein R' is hydrogen.
7. The method of claim 1 wherein R' is methyl.
8. The method of claim 1 wherein R' is ethyl.
9. The method of claim 1 wherein R' is hydroxymethyl.

* * * * *